(12) United States Patent
Ayer

(10) Patent No.: US 6,976,981 B2
(45) Date of Patent: Dec. 20, 2005

(54) OSMOTIC DELIVERY SYSTEM WITH MEMBRANE PLUG RETENTION MECHANISM

(75) Inventor: Rupal Ayer, Santa Clara, CA (US)

(73) Assignee: Alza Corporation, Mountain View, CA (US)

( * ) Notice: Subject to any disclaimer, the term of this patent is extended or adjusted under 35 U.S.C. 154(b) by 312 days.

(21) Appl. No.: 09/858,631

(22) Filed: May 17, 2001

(65) Prior Publication Data

US 2001/0021822 A1 Sep. 13, 2001

Related U.S. Application Data

(62) Division of application No. 09/217,823, filed on Dec. 22, 1998, now Pat. No. 6,270,787.
(60) Provisional application No. 60/068,987, filed on Dec. 29, 1997.

(51) Int. Cl.[7] ............................. A61K 9/52; A61F 2/02
(52) U.S. Cl. ............................. 604/890.1; 604/890.1; 604/891.1; 604/892.1; 424/468; 424/469; 424/470; 424/471; 424/472; 424/473; 424/422; 424/423; 424/424; 424/425; 424/426
(58) Field of Search .......................... 604/890.1, 891.1, 604/892.1; 424/468–473, 422–426

(56) References Cited

U.S. PATENT DOCUMENTS

| | | | |
|---|---|---|---|
| 3,732,865 A | 5/1973 | Higuchi et al. |
| 3,845,770 A | 11/1974 | Theeuwes et al. |
| 3,916,889 A | 11/1975 | Russell |
| 3,929,132 A | 12/1975 | Higuchi |
| 3,995,631 A | 12/1976 | Higuchi et al. |
| 3,995,632 A | 12/1976 | Nakano et al. |
| 4,111,202 A | 9/1978 | Theeuwes |
| 4,111,203 A | 9/1978 | Theeuwes |
| 4,203,439 A | 5/1980 | Theeuwes |
| 4,243,030 A | 1/1981 | Lynch et al. |
| 4,340,054 A | 7/1982 | Michaels |
| 4,373,527 A | 2/1983 | Fischell |
| 4,439,196 A | 3/1984 | Higuchi |
| 4,552,561 A | 11/1985 | Eckenhoff et al. |
| 4,639,244 A | 1/1987 | Rizk et al. |
| 4,865,845 A | 9/1989 | Eckenhoff et al. |
| 4,874,388 A | 10/1989 | Wong et al. |
| 5,137,727 A | 8/1992 | Eckenhoff |
| 5,223,265 A | 6/1993 | Wong |
| 5,279,608 A | 1/1994 | Cherif Cheikh |
| 5,308,348 A | 5/1994 | Balaban et al. |
| 5,312,389 A | 5/1994 | Theeuwes et al. |
| 5,312,390 A | 5/1994 | Wong |
| 5,456,679 A | 10/1995 | Balaban et al. |
| 5,728,396 A | 3/1998 | Peery et al. |
| 6,113,938 A | 9/2000 | Chen et al. |
| 6,270,787 B1 | 8/2001 | Ayer |

FOREIGN PATENT DOCUMENTS

| | | |
|---|---|---|
| WO | WO 95/35131 | 12/1995 |
| WO | WO 96/39987 | 12/1996 |
| WO | WO 97/27840 | 8/1997 |

Primary Examiner—Russell Travers
(74) Attorney, Agent, or Firm—TraskBritt

(57) ABSTRACT

An osmotic delivery system has a membrane plug retention mechanism which can also be used to control the delivery rate of a beneficial agent from the osmotic delivery system. The osmotic delivery device includes an implant capsule containing a beneficial agent and an osmotic agent. Holes are formed along a side wall of the implant capsule at an open end of the capsule. When the membrane plug is inserted into the open end of the capsule, the membrane material swells into the holes in the capsule side wall creating a large frictional force which prevents expulsion of the membrane plug. A beneficial agent delivery rate of the osmotic delivery system is controllable by varying the size and number of the holes to change the amount of exposed surface area of the membrane plug. An increase in the surface area of the membrane plug exposed to the exterior environment causes a corresponding increase in the liquid permeation rate of the membrane and thus, increases the beneficial agent delivery rate.

9 Claims, 2 Drawing Sheets

OSMOTIC DELIVERY SYSTEM WITH MEMBRANE PLUG RETENTION MECHANISM

This application is a divisional of application Ser. No. 09/217,823, filed on Dec. 22, 1998 now U.S. Pat. No. 6,270,787, issued Aug. 7, 2001, which claims the benefit under Title 35, United States Code, §119(e) of U.S. Provisional application No. 60/068,987 filed on Dec. 29, 1997.

BACKGROUND OF THE INVENTION

1. Field of the Invention

The present invention relates to osmotic delivery systems for delivering beneficial agents, and more particularly, to an osmotic delivery system having an osmotic engine and a membrane plug allowing fluid to pass into the osmotic engine.

2. Description of the Related Art

Controlled delivery of beneficial agents, such as drugs, in the medical and veterinary fields has been accomplished by a variety of methods. One method for controlled prolonged delivery of beneficial agents involves the use of osmotic delivery systems. These systems can be implanted within a body of a human or animal to release beneficial agents in a controlled manner over a preselected time or administration period. In general, osmotic delivery systems operate by imbibing liquid from the outside environment and releasing corresponding amounts of the beneficial agent.

A known osmotic delivery system, commonly referred to as an "osmotic pump," generally includes some type of a capsule or enclosure having a semipermeable portion which selectively passes water into an interior of the capsule containing a water-attracting osmotic agent. In one known osmotic delivery system, the walls of the capsule are substantially impermeable to items within and outside the capsule. A membrane plug is inserted into one end of the capsule and acts as the semipermeable portion to allow water to pass into the interior of the capsule. The difference in osmolarity between the water-attracting osmotic agent and the environment surrounding the capsule causes water to pass through the membrane plug into the capsule which in turn causes the beneficial agent within the capsule to be delivered through a delivery orifice. The water-attracting osmotic agent may be the beneficial agent delivered to the patient; however, in most cases, a separate osmotic agent is used specifically for its ability to draw water into the capsule.

When a separate osmotic agent is used, the osmotic agent may be separated from the beneficial agent within the capsule by a movable dividing member or piston. The structure of the capsule is such that the capsule does not expand when the osmotic agent takes in water and expands. As the osmotic agent expands, it causes the piston to move and the beneficial agent to be discharged through the delivery orifice at the same rate as the liquid (which is typically water), enters the osmotic agent by osmosis. Osmotic delivery systems may be designed to deliver a beneficial agent at a controlled constant rate, a varying rate, or in a pulsatile manner.

In the known osmotic delivery systems, an osmotic tablet is generally used as the osmotic agent and is placed inside the capsule adjacent the piston. The membrane plug is placed in an opening in the capsule through which the tablet and piston are inserted. Known membrane plugs are typically cylindrical members which seal the interior of the capsule from the exterior environment, permitting only certain liquid molecules from the environment of use to permeate through the membrane plug into the interior of the capsule. The rate that the liquid permeates through the membrane plug controls the rate at which the osmotic agent expands and drives the beneficial agent from the delivery system through the delivery orifice. The rate of delivery of the beneficial agent from the osmotic delivery system may be controlled by varying the size of the beneficial agent delivery orifice, the osmotic material, a size and shape of the membrane plug, or the permeability coefficient of the membrane plug.

The permeability coefficient of a membrane plug is dependent on the particular material or combination of materials used in the plug. Thus, the delivery rate of the beneficial agent may be controlled by forming the same configuration membrane plug from different semipermeable materials, these having permeability coefficients which result in delivery of the beneficial agent at a desired delivery rate. One problem associated with obtaining different permeation rates in this manner is that a different membrane material must be used for every system which has a different desired beneficial agent delivery rate, thus requiring the purchase of many different membrane materials and the manufacture of many different membrane plugs.

Many osmotic delivery systems which use membrane plugs have problems with expulsion of the membrane plug from the capsule. Expulsion may occur after the beneficial agent has been completely delivered while the osmotic agent continues to draw water into the capsule and forces the membrane plug out of the capsule. Some osmotic delivery systems use glues or adhesives to prevent the capsule from leaking and to ensure that the membrane plug remains in place in order to prevent harmful materials from the interior of the capsule from leaking into the surrounding environment. In addition to adding a manufacturing step and increasing costs, applying an adhesive to the membrane plugs may affect the rate of permeation.

Membrane plugs used in systems which are designed to deliver a beneficial agent at delivery rates which allow complete delivery of the beneficial agent in time periods from about 1 day to 2 weeks are particularly susceptible to membrane expulsion problems. These rapid delivery membranes swell due to water uptake within hours of implantation and become slippery and sponge-like. The rapid swelling of such membranes tends to cause the membranes to be expelled from the capsule.

Because of the above-identified problems associated with current osmotic delivery system membrane plugs, it is difficult and expensive to provide osmotic delivery systems which administer beneficial agents at different desired delivery rates and prevent expulsion of the membrane plug.

SUMMARY OF THE INVENTION

In accordance with the present invention, an osmotic implant has a membrane plug which swells into holes in the side wall of the capsule to lock the membrane in place.

According to one aspect of the present invention, an osmotic delivery device includes a delivery device capsule having a substantially cylindrical side wall, a first end having a beneficial agent delivery orifice, and a second open end. A separating member is positioned within the delivery device capsule and is movable in a longitudinal direction within the delivery device capsule to dispense the beneficial agent. An osmotic engine is positioned adjacent one side of the separating member. A plurality of openings is formed in the substantially cylindrical side wall adjacent the second open end of the delivery device capsule. A membrane plug is positioned within the second open end of the delivery device capsule and covers each of the plurality of openings in the substantially cylindrical side wall. The membrane plug is retained in the capsule by the plurality of openings.

In accordance with a further aspect of the invention, the membrane plug is formed of a material which swells causing a portion of the membrane plug to extend into the openings in the side wall increasing friction between the membrane plug and the delivery device capsule and preventing expulsion of the membrane plug from the delivery device capsule.

In accordance with another aspect of the present invention, an osmotic delivery device includes a delivery device body containing a beneficial agent to be delivered through a delivery orifice of the delivery device body and an osmotic agent for drawing external liquids into the delivery device body to cause the beneficial agent to be delivered. A membrane plug is secured in an open end of the delivery device body and allows the external liquids to pass through the membrane plug into the delivery device body. The membrane plug is secured in the open end of the delivery device body by a plurality of holes formed in the delivery device body around the open end of the delivery device body. The membrane plug is expandable to extend into the plurality of holes to prevent expulsion of the membrane plug from the delivery device body.

According to an additional aspect of the present invention, an implantable osmotic beneficial agent delivery device with a controllable beneficial agent delivery rate includes a substantially cylindrical body having a beneficial agent delivery orifice and an open end. A plurality of openings is formed in a side wall of the substantially cylindrical body at the open end. The plurality of openings is of a size and number determined to achieve a predetermined beneficial agent delivery rate. A membrane plug is received in the open end of the body and covers the plurality of openings.

In accordance with another additional aspect of the present invention, a method of retaining a membrane plug in an implantable osmotic device includes steps of forming a substantially cylindrical membrane plug; forming holes in the side wall of a capsule adjacent an open end of the capsule; inserting the substantially cylindrical membrane plug into the open end of the capsule such that the membrane plug covers the holes formed in the side wall; and causing the membrane plug to swell into the holes in the side wall to retain the membrane plug in the capsule.

The present invention provides the advantages of improved membrane retention and the ability to achieve a desired beneficial agent delivery rate by varying a number and size of the membrane retention openings.

BRIEF DESCRIPTION OF THE DRAWINGS

The invention will be described in greater detail with reference to the accompanying drawings in which like elements bear like reference numerals, and wherein.

DESCRIPTION OF THE PREFERRED EMBODIMENT

Figure 1:
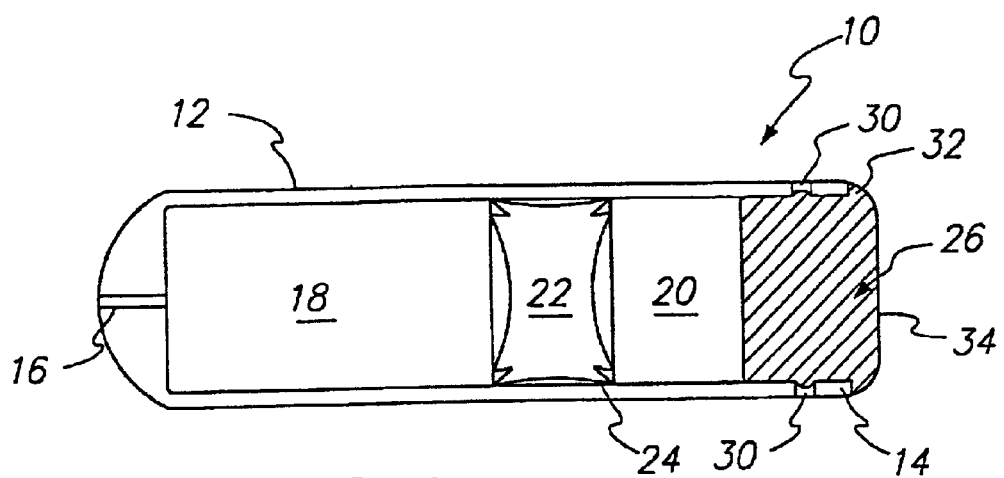
FIG. 1 is a side cross-sectional view of an osmotic drug delivery device according to the present invention.

The present invention relates to an osmotic delivery system for controlled delivery of a beneficial agent. The osmotic drug delivery device 10, as illustrated in FIG. 1, includes an elongated substantially cylindrical enclosure or capsule 12 having an open end 14. An end of the capsule 12 opposite the open end 14 has one or more delivery ports 16 for delivering a beneficial agent contained within a first chamber 18 of the osmotic delivery device 10. The elongated capsule 12 is formed of a material which is sufficiently rigid to withstand expansion of an osmotic agent contained within a second chamber 20 of the delivery device 10 without changing size or shape. The elongated capsule 12 is preferably substantially impermeable to fluids in the environment as well as to ingredients contained within the osmotic delivery device 10 such that the migration of such materials into or out of the device through the impermeable material of the capsule is so low so as to have substantially no adverse impact on the function of the osmotic delivery device.

The osmotic agent in the second chamber 20 of the capsule 12 is separated from the beneficial agent in the first chamber 18 by a movable separating member or piston 22. The movable separating member or piston 22 is a substantially cylindrically member which is configured to fit within the capsule 12 in a sealed manner which allows the piston to slide along a longitudinal direction within the capsule. The piston 22 preferably is formed of a resilient material which is impermeable to the compositions within the capsule and includes annular protrusions 24 which form a seal with the inner surface of the capsule 12.

As illustrated in FIG. 1, the drug delivery device 10 of one embodiment of the present invention includes a membrane plug 26, which is inserted in the open end 14 of the capsule 12 after placing the osmotic agent within the second chamber 20 of the capsule. The membrane plug 26 allows liquid to pass from an environment of use into the capsule 12 to cause the osmotic agent to swell. However, the material forming the semipermeable membrane plug 26 is largely impermeable to the materials within the capsule 12 and to other ingredients within the environment of use.

The configuration of the osmotic delivery system membrane plug 26 according to the present invention dictates the liquid permeation rate through the membrane plug, which, in turn, controls the delivery rate of a beneficial agent from the osmotic delivery system. The liquid permeation rate of a particular membrane plug depends on both the membrane material and the membrane shape.

Figure 2:
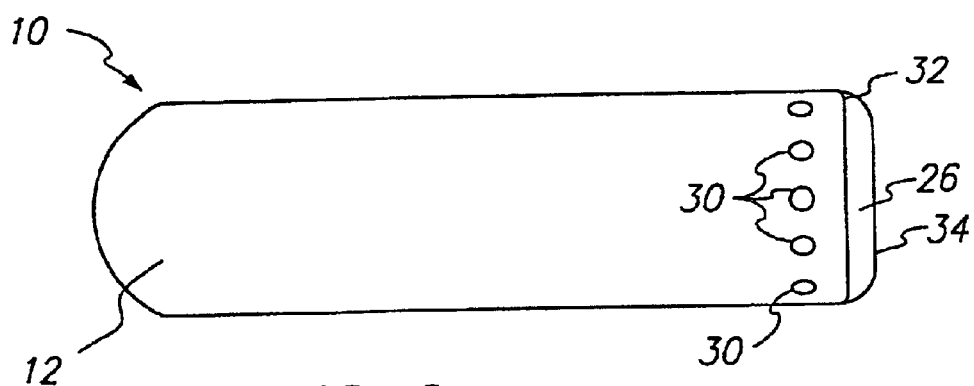
FIG. 2 is a side elevational view of the osmotic drug delivery device of FIG. 1.

FIG. 2 illustrates a side view of an osmotic drug delivery device 10 according to one embodiment of the present invention having a membrane plug 26 and a plurality of holes 30 in the capsule 12 for retaining the membrane plug 26 and controlling the beneficial agent delivery rate. The semipermeable membrane plug 26 is cylindrically shaped, and has a tight interference fit between an outer sealing surface of the membrane plug 26 and the capsule 12. In accordance with alternative embodiments of the invention, the membrane plug 26 may also include ribs extending from an outer surface of the membrane plug 26, or may include other configurations such as threads, glue, adhesives, ridges, lips, or other devices which seal the membrane plug to the interior walls of the capsule 12 to prevent leakage. The ribs may engage correspondingly shaped grooves in the interior walls of the capsule 12. The fit between the membrane plug 26 and the capsule 12 is preferably an interference fit which prevents significant salt leakage.

An inwardly directed annular lip may also be provided on the interior wall of the capsule 12 at the open end 14 to provide additional retention of the membrane. The membrane plug 26 is intended for at least partial insertion into the open end 14 of the capsule 12, and the tight interference fit prevents liquid and other substances in the environment of use, besides the permeation liquid, from entering the osmotic delivery device 10 while also preventing materials from the inside of the delivery system from leaking or escaping to the environment of use.

The membrane plug 26 includes a stop surface 32 which extends radially from the plug and abuts the end wall of the capsule 12 when the membrane plug is fully inserted. Alternatively, the membrane plug 26 need not have a stop surface 32 and the plug may be inserted entirely within the open end 14 of the capsule 12 of an osmotic delivery system. Likewise, the membrane plug 26 may be partially inserted into the open end 14 of the osmotic delivery system capsule 12.

Because at least a portion of the membrane plug 26 is within the capsule, only a portion of the membrane plug 26 is exposed to liquids in the environment of use. In the embodiment of the present invention illustrated in FIGS. 1 and 2, an end surface 34 of the semipermeable membrane is exposed to liquids in the environment of use. In addition, the portions of the membrane adjacent the holes 30 in the side wall of the capsule 12 are exposed to liquids in the environment. The end surface 34 preferably has smoothed or curved corners which are more acceptable for implantation than sharp edges. The outer diameter of the end surface 34, measured perpendicular to the longitudinal center axis of the delivery device 10, is approximately equal to that of an external diameter of the osmotic delivery device 10, such that the interface between the capsule and the liquid surface of the body 32 is void of abrupt edges, ridges, or sharp corners.

As shown in FIG. 2, the plurality of holes 30 is spaced around the open end 14 of the capsule 12. The holes 30 allow the membrane plug 26 to swell into the holes creating a large frictional force between the membrane plug and the interior capsule walls which prevents membrane plug expulsion. The frictional force between the capsule 12 and the membrane plug 26 is directly related to the number, placement, and shapes of the holes 30 in the capsule wall and the amount the plug material expands into the holes. The plurality of holes 30 may be sized and arranged to achieve a desired frictional force, however, each of the holes should be entirely covered by the membrane plug 26 so that osmotic agent leakage cannot occur. For example, between two and twenty holes may be provided of varying diameters. The number of holes 30 may also be greater than 20 for large diameter capsules 12 as long as the integrity of the capsule is maintained.

The plurality of holes 30 in the capsule wall also increases the exposed membrane plug surface area, thus increasing the liquid permeation rate through the membrane plug. The increased exposed area of the membrane plug will shorten the start-up period for beginning beneficial agent delivery over an identical system without the holes 30.

The liquid permeation rate dV/dt through a semipermeable membrane in an osmotic delivery system depends on the liquid permeability and shape of the membrane. The liquid permeation rate dV/dt for a conventional capsule without holes is determined by the formula:

$$dV/dt = k\pi\left(\frac{A}{t}\right)$$

$$\text{Where,} \quad A = \frac{\pi D_m^2}{4}$$

$D_m$ is the diameter of the exposed end surface 34 of the membrane plug and k is a constant which takes into account the liquid permeation rate and thickness of a membrane wall in a hollow membrane plug or the length for a solid membrane plug.

For an osmotic delivery device according to the present invention with a plurality of circular holes 30, the liquid permeation rate dV/dt is determined by the formula:

$$dV/dt = k\pi\left(\frac{A}{t}\right)$$

$$\text{Where,} \quad A = \frac{\pi D_m^2}{4} + \# \text{ of holes}\left(\frac{\pi D_h^2}{4}\right)$$

$D_m$ is the diameter of the exposed membrane plug end surface 34, $D_h$ is the diameter of the holes 30, and k is the constant taking into account the membrane plug material and thickness or length.

In the embodiment of FIG. 1, the liquid permeation rate dV/dt is also affected by the longitudinal position of the holes 30 on the capsule. The shorter the distance the liquid must travel through the membrane, the faster the liquid will permeate the membrane. Accordingly, the closer the holes 30 are to the end of the membrane plug adjacent to second chamber 20, the faster the release rate.

As can be seen from the foregoing, the liquid permeation rate, and thus, the beneficial agent delivery rate, can be controlled by changing the diameter and/or number of the holes 30 without the need to change the overall geometry of the osmotic delivery device 10 or the membrane plug 26. The delivery rate can also be controlled by varying the longitudinal position of the holes.

Figure 3:
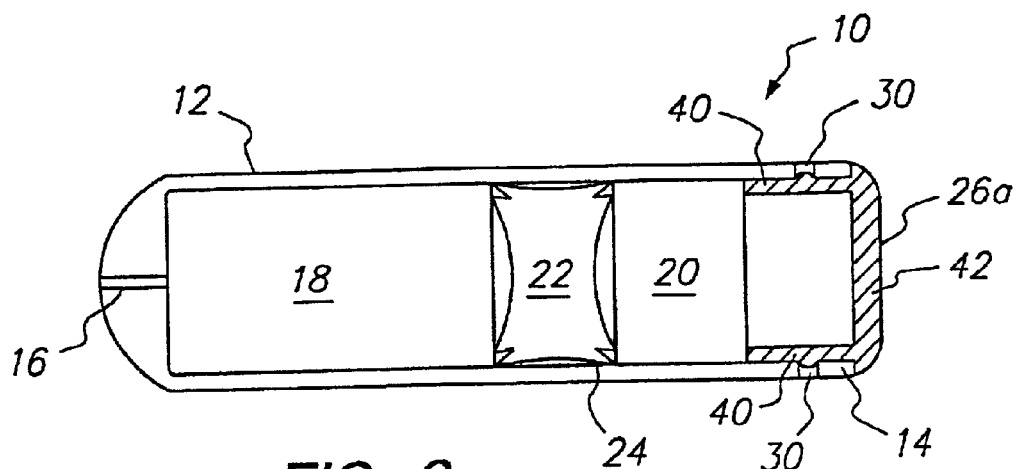
FIG. 3 is a side cross-sectional view of an osmotic drug delivery device having an alternative embodiment of a membrane plug.

An alternative embodiment of the invention illustrated in FIG. 3 includes a membrane plug 26a having a hollow interior and a substantially constant thickness cylindrical side wall 40 and end wall 42. The hollow membrane plug 26a is particularly useful in rapid delivery systems for delivery of a beneficial agent over a short period of time such as 1 to 42 days. In this embodiment, the beneficial agent delivery rate can be controlled by changing the diameter and/or number of the holes 30. However, the delivery rate generally does not change when the longitudinal position of the holes 30 is varied because the distance that the permeating liquid travels through the constant thickness side wall 40 is the same.

In the above-described manner, the liquid permeation rate dV/dt through the membrane plug 26 can be controlled simply and efficiently by forming holes 30 in the side walls of the capsule 12. This is advantageous because the same membrane plug 26 can be used to form osmotic delivery systems with different liquid permeation rates. A different membrane material need not be used for every system which has a different desired beneficial agent delivery rate, and biocompatibility and toxicity tests need only be performed on one semipermeable material.

The semipermeable membrane plug 26 is preferably injection molded. However, the semipermeable body may be fashioned by a different process. For example, the semipermeable body may also be made from extrusion, injection molding, rotational molding, thermoforming, compression molding, and other known casting processes.

FIGS. 1–3 illustrate two examples of osmotic delivery devices 10 according to the present invention. The configurations illustrated in the figures are examples of osmotic delivery devices and are not to be construed as limiting the present invention. The present invention is generally applicable to all osmotic delivery devices having any number of shapes, and to all such devices administered in humans and animals in any variety of methods such as oral, ruminal, and implantable osmotic delivery techniques.

Figure 4:
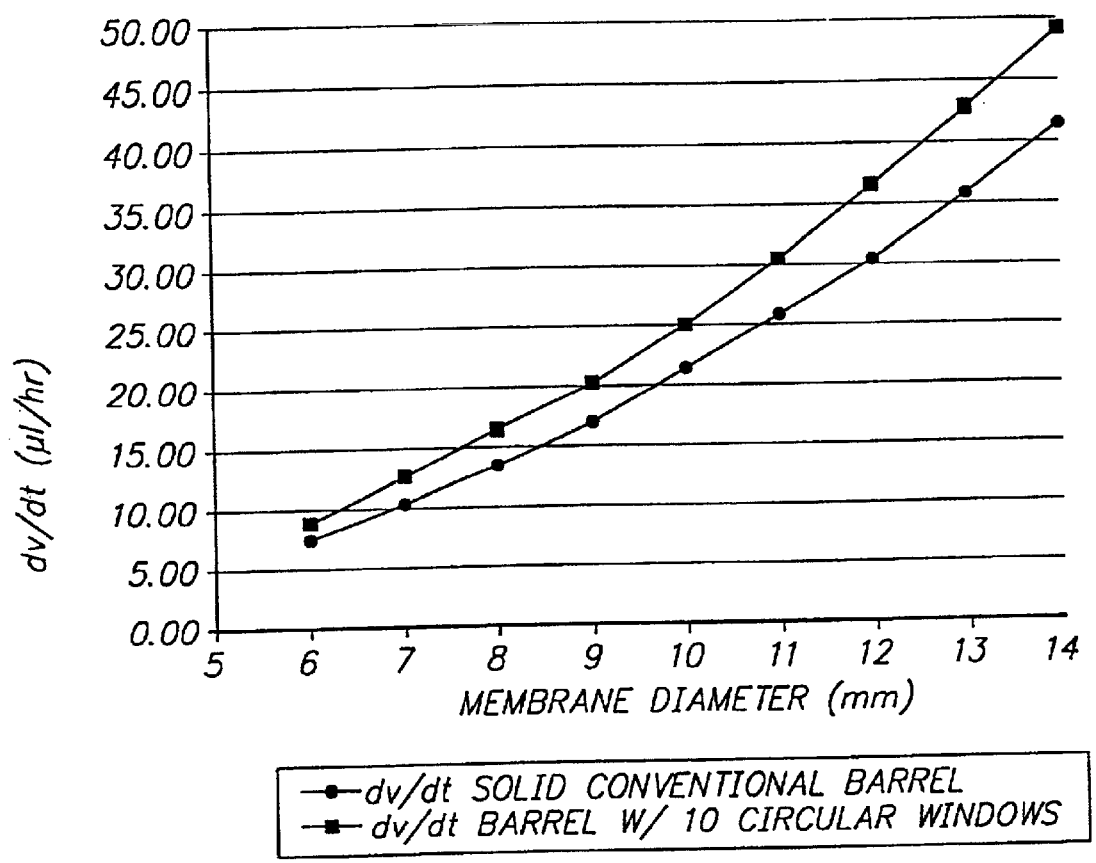
FIG. 4 is a graph comparing the beneficial agent delivery rate of the osmotic drug delivery device according to the present invention to an osmotic drug delivery device with a conventional capsule.

FIG. 4 shows the beneficial agent release rate for osmotic delivery devices having a conventional barrel without holes compared to the release rate for the osmotic delivery devices according to the present invention. As shown in FIG. 4, the release rate is increased by between approximately 1 and 10 ml/hr by the addition of 10 circular holes around the perimeter of the capsule's open end. The diameters of the holes 30 in the delivery device tested were approximately 14 percent of the diameter of the membrane. The amount of increase in the release rate depends in part on the diameter of the membrane retention holes.

Semipermeable compositions suitable for the semipermeable membrane plug 26 are well known in the art, examples of which are disclosed in U.S. Pat. No. 4,874,388, the entire disclosure of which is incorporated herein by reference. Such possible semipermeable materials from which the membrane plug 26 can be made include, but are not limited to, for example, Hytrel® polyester elastomers (DuPont), cellulose esters, cellulose ethers, and cellulose ester-ethers, water flux-enhanced ethylene-vinyl acetate copolymers, semipermeable membranes made by blending a rigid polymer with water-soluble low molecular weight compounds, and other semipermeable materials well known in the art. The above cellulosic polymers have a degree of substitution, D.S., on the anhydroglucose unit, from greater than 0 up to 3 inclusive. By "degree of substitution" or "D.S." is meant the average number of hydroxyl groups originally present on the anhydroglucose unit comprising the cellulose polymer that are replaced by a substituting group. Representative materials include, but are not limited to, one selected from the group consisting of cellulose acylate, cellulose diacylate, cellulose triacylate, cellulose acetate, cellulose diacetate, cellulose triacetate, mono-, di-, and tricellulose alkanylates, mono-, di-, and tricellulose aroylates, and the like. Exemplary cellulosic polymers include cellulose acetate having a D.S. up to 1 and an acetyl content up to 21%; cellulose acetate having a D. S. of 1 to 2 and an acetyl content of 21% to 35%; cellulose acetate having a D.S. of 2 to 3 and an acetyl content of 35% to 44.8%, and the like. More specific cellulosic polymers include cellulose propionate having a D.S. of 1.8 and a propionyl content of 39.2% to 45% and a hydroxyl content of 2.8% to 5.4%; cellulose acetate butyrate having a D.S. of 1.8 and an acetyl content of 13% to 15% and a butyryl content of 34% to 39%; cellulose acetate butyrate having an acetyl content of 2% to 29%, a butyryl content of 17% to 53%, and a hydroxyl content of 0.5% to 4.7%; cellulose acetate butyrate having a D.S. of 1.8, an acetyl content of 4%, and a butyryl content of 51%; cellulose triacylates having a D.S. of 2.9 to 3 such as cellulose trivalerate, cellulose trilaurate, cellulose tripalmitate, cellulose trisuccinate, and cellulose trioctanoate; cellulose diacylates having a D.S. of 2.2 to 2.6 such as cellulose disuccinate, cellulose dipalmitate, cellulose dioctanoate, cellulose dipentate; coesters of cellulose such as cellulose acetate butyrate and cellulose, cellulose acetate propionate, and the like.

Other materials for the membrane plug 26 are polyurethane, polyetherblockamide (PEBAX®, commercially available from ELF ATOCHEM, Inc.), and injection-moldable thermoplastic polymers with some hydrophilicity such as ethylene vinyl alcohol (EVA). In general, the membrane plug 26 is made from semipermeable materials having a water uptake ranging from 1% to 80% but preferably less than 50%. The composition of the semipermeable membrane plug 26 is permeable to the passage of external liquids such as water and biological liquids, and it is substantially impermeable to the passage of beneficial agents, osmopolymers, osmagents, and the like.

Materials which may be used for the capsule 12 must be sufficiently strong to ensure that the capsule will not leak, crack, break, or distort under stresses to which it is subjected during implantation or under stresses due to the pressures generated during operation. The capsule 12 may be formed of chemically inert and biocompatible, natural or synthetic materials which are known in the art. The capsule material is preferably a non-bioerodible material which remains in the patient after use, such as titanium or a titanium alloy, and is largely impermeable to materials within and outside the capsule. However, the material of the capsule 12 may alternatively be a bioerodible material which bioerodes in the environment after dispensing of the beneficial agent. Generally, preferred materials for the capsule 12 are those acceptable for animal and human implants.

In general, typical materials of construction suitable for the capsule 12 according to the present invention include non-reactive polymers or biocompatible metals or alloys. The polymers include acrylonitrile polymers such as acrylonitrile-butadiene-styrene terpolymer, and the like; halogenated polymers such as polytetrafluoroethylene, polychlorotrifluoroethylene, copolymer tetrafluoroethylene and hexafluoropropylene; polyimide; polysulfone; polycarbonate; polyethylene; polypropylene; polyvinylchloride-acrylic copolymer; polycarbonate-acrylonitrile-butadiene-styrene; polystyrene; and the like. Metallic materials useful for the capsule 12 include stainless steel, titanium, platinum, tantalum, gold, and their alloys, as well as gold-plated ferrous alloys, platinum-plated ferrous alloys, cobalt-chromium alloys and titanium nitride coated stainless steel.

The capsule 12 may be formed from any of the wall-forming materials disclosed above by the use of a mold, with the materials applied either over the mold or inside the mold, depending on the mold configuration. Any of the wide variety of techniques known in the pharmaceutical industry may be used to form the capsule 12.

In general, materials suitable for use in the movable separating member or piston 22 are elastomeric materials including the non-reactive polymers listed above, as well as elastomers in general, such as polyurethanes and polyamides, chlorinated rubbers, styrene-butadiene rubbers, and chloroprene rubbers.

The osmotic agent is a liquid-attracting agent used to drive the flow of the beneficial agent. The osmotic agent may be an osmagent, an osmopolymer, or a mixture of the two. Species which fall within the category of osmagent, i.e., the non-volatile species which are soluble in water and create the osmotic gradient driving the osmotic inflow of water, vary widely. Examples are well known in the art and include magnesium sulfate, magnesium chloride, potassium sulfate, sodium chloride, sodium sulfate, lithium sulfate, sodium phosphate, potassium phosphate, d-mannitol, sorbitol, inositol, urea, magnesium succinate, tartaric acid, raffinose, and various monosaccharides, oligosaccharides and polysaccharides such as sucrose, glucose, lactose, fructose, and dextran, as well as mixtures of any of these various species.

Species which fall within the category of osmopolymer are hydrophilic polymers that swell upon contact with water, and these vary widely as well. Osmopolymers may be of plant or animal origin, or synthetic, and examples of osmopolymers are well known in the art. Examples include: poly(hydroxy-alkyl methacrylates) with molecular weight of 30,000 to 5,000,000, poly(vinylpyrrolidone) with molecular weight of 10,000 to 360,000, anionic and cationic hydrogels, polyelectrolyte complexes, poly(vinyl alcohol) having low acetate residual, optionally cross-linked with glyoxal, formaldehyde, or glutaraldehyde and having a degree of polymerization of 200 to 30,000, a mixture of methylcellulose, cross-linked agar and carboxymethylcellulose, a mixture of hydroxypropl methycellulose and sodium carboxymethylcellulose, polymers of N-vinyllactams, polyoxyethylene-polyoxypropylene gels, polyoxybutylene-polyethylene block copolymer gels, carob gum, polyacrylic gels, polyester gels, polyuria gels, polyether gels, polyamide gels, polypeptide gels, polyamino acid gels, polycellulosic gels, carbopol acidic carboxy polymers having molecular weights of 250,000 to 4,000,000, Cyanamer® polyacrylamides, cross-linked indene-maleic anhydride polymers, Good-Rite® polyacrylic acids having molecular weights of 80,000 to 200,000, Polyox® Polyethylene oxide polymers having molecular weights of 100,000 to 5,000,000, starch graft copolymers, and Aqua-Keeps acrylate polymer polysaccharides.

The osmotic agent may be a solid osmotic tablet or a fluid osmotic agent. The osmotic tablet may be formed in many different conceivable shapes, textures, densities, and consistencies and still be within the confines of the present invention. The osmotic agent may be manufactured by a variety of techniques, many of which are known in the art. In one such technique, the osmotically active agent is prepared as solid or semisolid formulation and pressed into pellets or tablets whose dimensions correspond to slightly less than the internal dimensions of the respective chambers which they will occupy in the capsule interior. Depending on the nature of the materials used, the agent and other solid ingredients which may be included may be processed prior to the formation of the pellets by such procedures as ballmilling, calendaring, stirring, or rollmilling to achieve a fine particle size and fairly uniform mixtures of each.

In assembling the osmotic delivery device 10 according to one preferred embodiment of the present invention, the capsule 12 is prepared by forming the plurality of holes 30 around the open end 14 of the capsule. The holes 30 may be formed by mechanical drilling, laser drilling, molding, or any other known method. Once the capsule 12 has been prepared with a plurality of holes 30 having a number and size to achieve a desired delivery rate of the beneficial agent, the piston 22 is inserted into the capsule 12. Once the osmotic agent pellet(s) or tablet(s) have been formed, they are placed inside the pre-formed capsule in the second chamber 20 on top of the piston 22. Then the membrane plug 26, according to one embodiment of the present invention, is placed into the open end 14 of the capsule 12 to close off and seal one end of the osmotic delivery system.

The delivery port 16 is an orifice formed by conventional techniques which are known in the art. Included among these methods are mechanical drilling, laser drilling, and molding. The capsule 12 contains at least one such delivery port 16, and in most configurations, one delivery port will suffice. However, two or more delivery ports 16 may be present without departing from the present invention. The dimensions of the port 16 in terms of both diameter and length will vary with the type of beneficial agent, the rate at which the beneficial agent is to be delivered, and the environment into which it is to be delivered. The considerations involved in determining the optimum dimensions of the delivery port for any particular capsule 12 or beneficial agent and the selection of the appropriate dimensions will be readily apparent to those skilled in the art.

According to one embodiment of the present invention, the beneficial agent contained in the first chamber 18 of the capsule 12 is a flowable composition such as a liquid, suspension, or slurry, and is typically poured into the first chamber 18 of the capsule after the osmotic agent and the piston 22 have been inserted. However, the first chamber 18 may also be filled through the open end prior to insertion of the piston.

The present invention applies to the administration of beneficial agents in general, which include any physiologically or pharmacologically active substance. Drug agents which may be delivered by the present invention include drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, proteins, enzymes, hormones, polynucleotides, nucleoproteins, polysaccharides, glycoproteins, lipoproteins, polypeptides, steroids, analgesics, local anesthetics, antibiotic agents, anti-inflammatory corticosteroids, ocular drugs and synthetic analogs of these species.

Examples of drugs which may be delivered by devices according to this invention include, but are not limited to, prochlorperzine edisylate, ferrous sulfate, aminocaproic acid, mecamylamine hydrochloride, procainamide hydrochloride, amphetamine sulfate, methamphetamine hydrochloride, benzamphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperzine maleate, anisindone, diphenadione erythrityl tetranitrate, digoxin, isofluorophate, acetazolamide, methazolamide, bendroflumethiazide, chloropromaide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17-S-estradiol, ethinyl estradiol, ethinyl estradiol 3-methyl ether, prednisolone, 17-α-hydroxyprogesterone acetate, 19-norprogesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, capropril, mandol, quanbenz, hydrochlorothiazide, ranitidine, flurbiprofen, fenufen, fluprofen, tolmetin, alclofenac, mefenamic, flufenamic, difuinal, nimodipine, nitrendipine, nisoldipine, nicardipine, felodipine, lidoflazine, tiapamil, gallopamil, amlodipine, mioflazine, lisinolpril, enalapril, enalaprilat, captopril, ramipril, famotidine, nizatidine, sucralfate, etintidine, tetratolol, minoxidil, chlordiazepoxide, diazepam, amitriptyline, and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatotropin, oxytocin, vasopressin, GRF, prolactin, somatostatin, lypressin, pancreozymin, luteinizing hormone, LHRH, LHRH agonists and antagonists, leuprolide, interferons, interleukins, growth hormones such as human growth hormone, bovine growth hormone and porcine growth hormone, fertility inhibitors such as the prostaglandins, fertility promoters, growth factors, coagulation factors, human pancreas hormone releasing factor, analogs and derivatives of these compounds, and pharmaceutically acceptable salts of these compounds, or their analogs or derivatives.

On the molecular level, the various forms of the beneficial agent may include uncharged molecules, molecular complexes, and pharmaceutically acceptable acid addition and base addition salts such as hydrochlorides, hydrobromides, acetate, sulfate, laurylate, oleate, and salicylate. For acidic compounds, salts of metals, amines or organic cations may be used. Derivatives such as esters, ethers and amides can also be used. A beneficial agent can be used alone or mixed with other agents. The beneficial agent may optionally include pharmaceutically acceptable carriers and/or additional ingredients such as antioxidants, stabilizing agents, permeation enhancers, etc.

According to other embodiments of the present invention, the capsule 12 may take different forms. For example, the delivery port 16 may be formed in a soft impermeable material delivery plug inserted into the capsule 12. In addition, the movable separating member or piston 22 may be a flexible member such as a diaphragm, partition, pad, flat sheet, spheroid, or rigid metal alloy, and may be made of any number of inert materials. Furthermore, the osmotic device may function without the piston 22, having simply an interface between the osmotic agent and the beneficial agent.

Animals to whom beneficial agents may be administered using systems of this invention include humans and other animals. The invention is of particular interest for application to humans and household, sport, and farm animals, particularly mammals. For the administration of beneficial agents to animals, the devices of the present invention may be implanted subcutaneously or intraperitoneally wherein aqueous body fluids are available to activate the osmotic agent. Devices of the invention may also be administered to the rumen of ruminant animals, in which embodiment the devices may further comprise a density element for maintaining the device in the rumen for extended periods of time of up to 120 days or longer. Density elements are well known in the art of drug delivery devices.

The delivery devices of this invention are also useful in environments outside of physiological or aqueous environments. For example, the delivery devices may be used in intravenous systems (attached to an IV pump or bag or to an IV bottle, for example) for delivering beneficial agents to an animal, primarily to humans. They may also be utilized in blood oxygenators, kidney dialysis and electrophoresis, for example. Additionally, delivery devices of the present invention may be used in the biotechnology area, such as to deliver nutrients or growth-regulating compounds to cell cultures. In such instances, activating mechanisms such as mechanical mechanisms are particularly useful. The beneficial agent may be any of the agents which are known to be delivered to the body of a human or an animal such as medicaments, vitamins, nutrients, or the like. The beneficial agent may also be an agent which is delivered to other types of aqueous environments such as pools, tanks, reservoirs, and the like. Included among the types of agents which meet this description are biocides, sterilization agents, nutrients, vitamins, food supplements, sex sterilants, fertility inhibitors and fertility promoters.

While the invention has been described in detail with reference to preferred embodiments thereof, it will be apparent to one skilled in the art that various changes can be made, and equivalents employed without departing from the invention.

I claim:

1. An osmotic delivery device comprising:
    a delivery device body containing a beneficial agent to be delivered through a delivery port at a closed end of the delivery device body and an osmotic agent for drawing external liquids into the delivery device body to cause the beneficial agent to be delivered; and
    an expandable, semipermeable membrane plug secured in an open end of the delivery device body and allowing the external liquids to pass through the membrane plug into the delivery device body, the membrane plug secured in the open end of the delivery device body by a plurality of holes formed in the delivery device body around the open end of the delivery device body, the membrane plug expandable to extend into the plurality of holes to prevent expulsion of the membrane plug from the delivery device body.

2. The osmotic delivery device according to claim 1, wherein the delivery device body further comprises a movable piston separating a first chamber containing the beneficial agent from a second chamber containing the osmotic agent and causing the beneficial agent to be delivered through the delivery port when the osmotic agent draws the external liquids through the membrane plug.

3. The osmotic delivery device according to claim 1, wherein external liquid is drawn into the delivery device body through the membrane plug by way of the open end of the delivery device body and the plurality of holes.

4. The osmotic delivery device according to claim 1, wherein the plurality of holes are cylindrical bores spaced in an annular manner around a side wall of the delivery device body adjacent the open end of the delivery device body.

5. The osmotic delivery device according to claim 1, wherein the delivery device body has a substantially cylindrical side wall and the plurality of holes are formed in the substantially cylindrical side wall.

6. The osmotic delivery device according to claim 5, wherein substantially cylindrical side wall includes an inwardly directed annular lip at the open end of the delivery device body which provides additional retention of the membrane plug in the delivery device body.

7. The osmotic delivery device according to claim 2, wherein the movable piston is movable longitudinally in a direction defined by a longitudinal axis passing through the delivery port and the open end of the delivery device.

8. The osmotic delivery device according to claim 1, wherein the membrane plug provides a semipermeable closure of the open end of the delivery device, the membrane plug allowing fluid to pass into an osmotic engine and preventing the osmotic engine from passing out of a capsule.

9. The osmotic delivery device according to claim 5, wherein the plurality of holes are cylindrical bores spaced in an annular manner around the side wall.

* * * * *